United States Patent

Harris et al.

[11] 3,972,880
[45] Aug. 3, 1976

[54] MORPHOLINE CONTAINING ESTERS OF THIENOBENZOPYRANS AND THIOPYRANOBENZOPYRANS

[75] Inventors: Louis Selig Harris, Richmond, Va.; Harry George Pars, Lexington, Mass.; Raj Kumar Razdan, Belmont, Mass.; John Clark Sheehan, Lexington, Mass.

[73] Assignee: Sharps Associates, Cambridge, Mass.

[22] Filed: Mar. 17, 1975

[21] Appl. No.: 558,640

Related U.S. Application Data

[60] Division of Ser. No. 448,401, March 5, 1974, which is a continuation-in-part of Ser. No. 212,820, Dec. 27, 1971, abandoned.

[52] U.S. Cl. ............ 260/247.1 P; 424/246; 424/248; 424/250; 424/267; 424/274; 424/275; 260/243 B; 260/268 TR; 260/326.35; 260/327 TH; 260/332.2 R
[51] Int. Cl.² ............................ C07D 495/04
[58] Field of Search .................. 260/247.1 P

[56] References Cited
UNITED STATES PATENTS
3,895,034  7/1975  Winn et al. .................. 260/332.2

*Primary Examiner*—Henry R. Jiles
*Assistant Examiner*—R. W. Ramsuer
*Attorney, Agent, or Firm*—Merriam, Marshall, Shapiro & Klose

[57] ABSTRACT

Novel thienobenzopyran and thiopyranobenzopyran esters represented by the formula

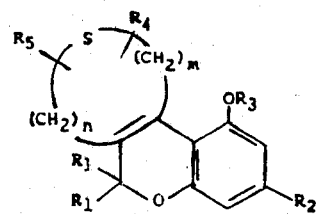

wherein $n$ is 0 to 3 and $m$ is 0 to 3 and $m + n = 2$ or 3, $R_1$ is lower alkyl, $R_2$ is alkyl or cycloalkyl-lower alkyl, $R_4$ is hydrogen or lower alkyl, $R_5$ is hydrogen or lower alkyl, and $R_3$ is

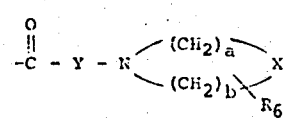

wherein Y is a straight or branched chain $C_1$ to $C_8$ alkylene, $R_6$ is hydrogen or a lower alkyl, $a$ is an integer from 1 to 4, $b$ is an integer from 1 to 4, X is $CH_2$, O, S or $NR_7$ wherein $R_7$ is hydrogen or lower alkyl, with the limitation that when X is O, S or $NR_7$, $a$ and $b$ each must be 2; and the acid addition salts thereof.

22 Claims, No Drawings

MORPHOLINE CONTAINING ESTERS OF THIENOBENZOPYRANS AND THIOPYRANOBENZOPYRANS

RELATED APPLICATIONS

This application is a division of application Ser. No. 448,401, filed Mar. 5, 1974, which is a continuation-in-part of our copending application Ser. No. 212,820 filed Dec. 27, 1971 now abandoned.

DETAILED DESCRIPTION OF THE INVENTION

This application relates to novel heterocyclic esters of thienobenzopyrans and thiopyranobenzopyrans and to methods of making and using the novel compounds.

More particularly, this invention relates to novel heterocyclic esters of chemical compounds which includes those designated as 7-alkyl (and 7-cycloalkyl-loweralkyl)-9-hydroxy-4,4-diloweralkyl-1,3-dihydro-4H-thieno[3,4-c] [1] benzopyrans; 7-alkyl (and 7-cycloalkyl-loweralkyl)-9-hydroxy-4,4-diloweralkyl-1,2-dihydro-4H-thieno[2,3-c] [1] benzopyrans; 8-alkyl (and 8-cycloalkyl-loweralkyl)-10-hydroxy-5,5-diloweralkyl-1,2-dihydro-4H,5H-thiopyrano[3,4-c] [1] benzopyrans and 8-alkyl (and 8-cycloalkyl-loweralkyl)-10-hydroxy-5,5-diloweralkyl-1,2-dihydro-3H,5H-thiopyrano[2,3-c] [1] benzopyrans; 8-alkyl (and 8-cycloalkyl-loweralkyl)10-hydroxy-5,5-diloweralky-3,4-dihydro-1H,5H,thiopyrano [4,3-c] [1] benzopyrans; 8-alkyl (and 8-cycloalkyl-loweralkyl)10-hydroxy-5,5-diloweralkyl-2,3-dihydro-4H,5H-thiopyrano [3,2-c] [1] benzopyran; and 7-alkyl (and 7-cycloalkyl-loweralkyl)-9-hydroxy-4,4-diloweralkyl-2,3-dihydro-4H-thieno[3,2-c] [1] benzopyran.

The compounds of this invention are represented by Formula I:

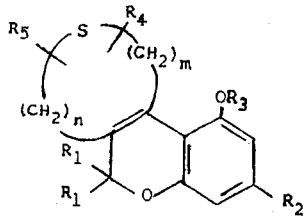

wherein $m$ is 0 to 3, $n$ is 0 to 3, and $n + m = 2$ or 3, $R_1$ is lower alkyl, $R_2$ is alkyl or cycloalkyl-loweralkyl, $R_4$ is hydrogen or lower alkyl, $R_5$ is hydrogen or lower alkyl, and $R_3$ is

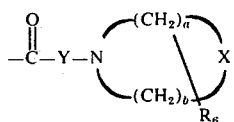

wherein Y is a straight or branched chain $C_1$ to $C_8$ alkylene, $R_6$ is hydrogen or lower alkyl, a is an integer from 1 to 4, b is an integer from 1 to 4, X is $CH_2$, O, S or $NR_7$ wherein $R_7$ is hydrogen or lower alkyl, with the limitation that when X is O, S or $NR_7$, a and b each must be 2; and the acid addition salts thereof. Particularly important are the compounds in which Y has two to five carbons. Those with three, four and five carbons for Y are the preferred group. In addition, the Y group should generally have at least two carbons in a chain between the carbonyl group and the nitrogen atom.

When m is one and n is one, the 1,3-dihydro-4H-thieno[3,4-c] [1] benzopyrans are represented by general Formula II:

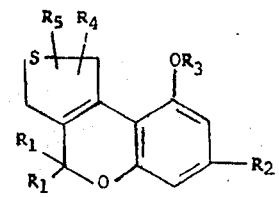

When $m$ is 2 and $n$ is zero, the 1,2-dihydro-4H-thieno-[2,3-c] [1] benzopyrans are represented by Formula III:

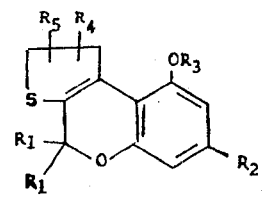

When $n$ is 2 and $m$ is zero, the 2,3-dihydro-4H-thieno-[3,2-c] [1] benzopyrans are represented by the general formula IV:

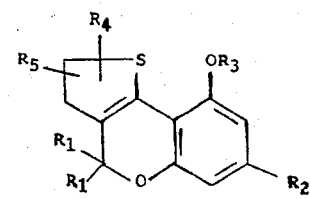

When n is 2 and m is one, the 3,4-dihydro-1H,5H-thiopyrano[4,3-c] [1] benzopyrans are represented by the general formula V:

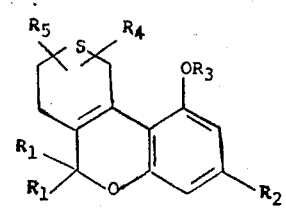

When n is 3 and m is zero, the 2,3-dihydro-4H,5H-thiopyrano[3,2-c] [1]benzopyrans are represented by the general formula VI:

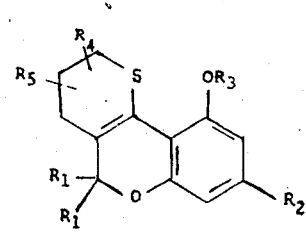

When *m* is two and *n* is one, the 1,2-dihydro-4H,5H-thiopyrano[3,4-c] [1] benzopyrans are represented by general Formula VII:

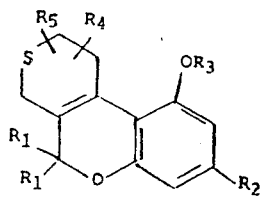
VII when *m* is three and *n* is zero, the 1,2-dihydro-3H,5H-thiopyrano[2,3-c] [1] benzopyrans are represented by Formula VIII:

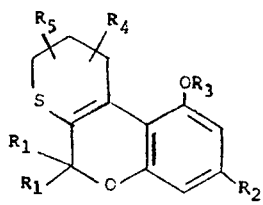
VIII wherein $R_1$, $R_2$, $R_3$, $R_4$ and $R_5$ have the meanings previously given herein.

As used herein, the term lower alkyl means saturated, monovalent aliphatic radicals, including straight and branched chain radicals of from one to six carbon atoms, as illustrated by, but not limited to methyl, ethyl, propyl, isopropyl, butyl, sec-butyl, amyl, hexyl and the like.

The term alkyl means saturated, monovalent aliphatic radicals, including straight and branched chain radicals of from one to twenty carbon atoms, as illustrated by, but not limited to methyl, n-amyl, n-hexyl, 2-heptyl, n-heptyl, 3-methyl-2-octyl, n-octyl, 2-nonyl, 2-tetradecyl, n-hexadecyl, 2-eicosanyl and the like.

The term cycloalkyl means cyclic, saturated aliphatic radicals of from three to eight carbon atoms, as illustrated by but not limited to cyclopropyl, cyclobutyl, 2-methylcyclobutyl, cyclohexyl, 4-methylcyclohexyl, cyclooctyl and the like.

The term acid addition salts means non-toxic salts prepared by reacting the basic esters of the thiopyranobenzopyrans or thienobenzopyrans with an organic or inorganic acid, or by reacting the pyran with the appropriate salt of the acid. Representative salts include the hydrochloride, hydrobromide, sulfate, bisulfate, acetate, valerate, oleate, laurate, borate, benzoate, lactate, phosphate, tosylate, citrate, maleate, succinate, tartrate and the like. Such salts are well known in the art and are considered to be pharmaceutically acceptable.

Particular compounds provided by the invention are those of the formula:

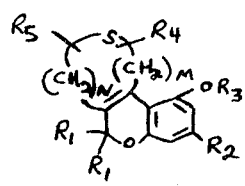

wherein *n* is 0 to 3, and *m* is 0 to 3 and $m + n = 2$ or 3, $R_1$ is a lower alkyl having 1 to 6 carbon atoms, $R_2$ is an alkyl having 1 to 20 carbon atoms or cycloalkyl-loweralkyl in which the cycloalkyl group has 3 to 8 carbon atoms and the lower alkyl group has 1 to 6 carbon atoms, $R_4$ is hydrogen or a lower alkyl having 1 to 6 carbon atoms, $R_5$ is hydrogen or a lower alkyl having 1 to 6 carbon atoms, and $R_3$ is

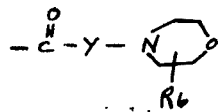

wherein Y is a straight or branched chain $C_1$ to $C_8$ alkylene, $R_6$ is hydrogen or a lower alkyl having 1 to 6 carbon atoms, and the nontoxic acid addition salts thereof.

The novel esters of this invention are prepared by reacting equimolar quantities of the corresponding thienobenzopyran or thiopyranobenzopyran with the appropriate acid or acid salt in the presence of a slight excess of a carbodiimide, such as dicyclohexylcarbodiimide, in a suitable solvent.

The reaction mixture is filtered to remove the by-product of dicyclohexylurea, and the solvent can be distilled off using a rotary evaporator. The residue can be directly crystallized from suitable solvents such as benzene/ether or the residue can be chromatographed and the desired material isolated from the appropriate chromatographic fractions. The basic esters obtained can be converted to acid addition salts, if desired, by methods well known in the art.

The starting thienobenzopyrans and thiopyranobenzopyrans are prepared by reacting the corresponding oxocompound of Formula IX with a lower alkyl magnesium halide as illustrated by the following reaction:

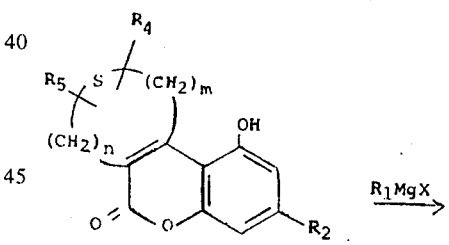

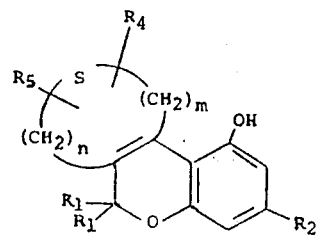

wherein *m*, *n*, $R_1$, $R_2$, $R_4$ and $R_5$ have the meanings given hereinabove, and X represents a reactive halogen. The reaction is carried out in an organic solvent inert under the conditions of the reaction. Suitable solvents are diethyl ether, dibutyl ether, tetrahydrofuran, anisole, pyridine and the like.

Many of the compounds of Formula X are disclosed in German Pat. application publication No. 2,041,610 dated Mar. 25, 1971 and in copending U.S. Pat. application Ser. No. 392,636 filed Aug. 29, 1973 now U.S. Pat. No. 3,895,034 issued July 15, 1975 which is incorporated herein by reference.

The pyrone of Formula IX can be prepared by reacting a compound of Formula XI with a 5-alkyl or 5-cycloalkylloweralkyl resorcinol (XII) as shown below:

$$\underset{\text{XI}}{\begin{array}{c}R_5\\ \diagup\\ S\\ \diagdown\\ (CH_2)_n\\ \diagdown\\ C\\ \diagup\\ CCOAlkyl\end{array}\begin{array}{c}R_4\\ \diagdown\\ (CH_2)_m\\ \diagup\\ C\\ \diagdown\\ O\end{array}} \;+\; \underset{\text{XII}}{\begin{array}{c}OH\\ \diagup\\ \diagdown\\ OH\quad R_2\end{array}} \;\longrightarrow\; \underset{\text{IX}}{\begin{array}{c}R_5\diagup S\diagdown (CH_2)_m\\ \diagup\qquad\diagdown OH\\ (CH_2)_n\\ \diagdown\qquad\diagup\\ O=\diagdown O\diagup R_2\end{array}}$$

wherein $m$, $n$, $R_2$, $R_4$ and $R_5$ have the previously assigned meaning.

The intermediate 5-alkyl or 5-cycloalkyl-loweralkyl-resorcinols of Formula XII are conveniently prepared by methods generally known in the art. (See U.S. Pat. No. 3,576,798).

The keto esters, alkyl 4-oxo-2,3,4,5-tetrahydrothiophene-3-carboxylate and alkyl 3-oxo-2,3,4,5-tetrahydrothiophene-2-carboxylate may be prepared by the procedure of Woodward and Eastman, *J. Am. Chem. Soc.* 68, 2229 (1946); alkyl 4-oxo-2,3,5,6-tetrahydro-4H-thiopyran-3-carboxylate by the method of G. M. Bennett and L. V. D. Scorah, *J. Chem. Soc.*, 194, (1927); and alkyl 3-oxo-2,3,4,5-tetrahydro-6H-thiopyran-2-carboxylate by the procedure of Leonard and Figueras, *J. Chem. Soc.*, 74, 917 (1952). Methyl 4-methyl-3-oxo-tetrahydrothiophene-2-carboxylate is disclosed in *Chemical Abstracts*, 63, 5491 (1965). Ethyl 5,5-dimethyl-3-oxo-tetrahydrothiophene-2-carboxylate is prepared by reacting diethyl 4,4-dimethyl-3-thiahexanedioate with potassium tertiary butoxide. 5-methyl-3-oxo-tetrahydrothiophene-2-carboxylate is formed by reacting diethyl 4-methyl-3-thiahexanedioate with potassium tertiary butoxide.

The compounds of Formula I are useful as mild tranquilizers at dosages of from 5.0 to 20 mg./kg. of body weight daily. While the compounds exhibit activity when administered either by the oral or intraperitoneal routes, the oral route is presently preferred.

The tranquilizing activity was established in a battery of standard tests described in *Psychopharmacology, A Ten Year Review*, Public Health Service Publication No. 1836, including overt behavior in mice, rats, dogs and monkeys, blocking fighting response in mice, blocking learning acquisition, etc.

1,2-Dihydro-5,5-dimethyl-8-(3-methyl-2-octyl)-10-[4-(piperidino)butyryloxy]-3H,5H-thiopyrano[2,3-c][1]benzopyran hydrochloride at an oral dose of 20 mg./kg. showed moderate activity in the mouse modified DOPA potentiation test (Everett, G.M., *Proc. First Internat. Sympos. Antidepressant Drugs, Excerpta Med. Int. Congr. Ser.* No. 122, 1966) indicating the compound has antidepressant activity. At an oral dose of 5 mg./kg. this compound caused a 74% reduction in spontaneous motor activity in the rat indicating that the compound induces sedative activity.

1,2-Dihydro-5,5-dimethyl-8-(3-methyl-2-octyl)-10-[2-methyl-4-(piperidino)butyryloxy]-3H,5H-thiopyrano [2,3-c] [1]benzopyran hydrochloride at an oral dose of 20 mg./kg. showed slight activity in the mouse modified DOPA potentiation test. At an oral dose of 10 mg./kg. this compound caused a 76% reduction in fighting behaviour in a mouse fighting test. (Tedeschi, R.E. et al., *J. Pharmacol. Exp. Therap.*, 125, 28 (1959) with modifications; response to footshock measured). The compound thus possesses antianxiety activity as well as tranquilization activity.

1,2-Dihydro-4,4-dimethyl-9-[4-morpholino)-butyryloxy]-7-(3-methyl-2-octyl)-4H-thieno[2,3-c] [1]benzopyran hydrochloride administered orally in a dose of 20 mg./kg., showed marked activity in the mouse modified DOPA potentiation test. At an oral dose of 10 mg./kg., it caused a 56% reduction in fighting behavior in the mouse fighting test. In the mouse hot plate test (G. Woolfe et al., *J. Pharmacol. Exper. Therap.*, 80, 300, 1944) at an oral dose of 50 mg./kg., it showed mild activity, causing a 44% increase in the pain threshold. In the audiogenic seizure test (Plotnikoff, *J. Pharmacol. Exp. Therap.*, 119, 234, 1957) at an oral dose of 100 mg./kg., it protected 100% of the mice from the convulsions. These activities indicate the compound is useful as an antidepressant, antianxiety (tranquilizer), analgesic, or anticonvulsant agent.

1,2-Dihydro-4,4-dimethyl-9-[4-piperidino)-butyryloxy]-7-(3-methyl-2-octyl)-4H-thieno[2,3-c] [1]benzopyran hydrochloride administered orally in a dose of 20 mg./kg., showed no activity in the mouse modified DOPA potentiation test. At an oral dose of 10 mg./kg., it caused a 50% reduction in fighting behavior in the mouse fighting test. In the acetic acid induced writhing test in mice (B.A. Whittle, *Brit. J. Pharmacol.*, 22, 246–253, 1964) it showed moderate activity, having an $ED_{50}$ of 24 mg./kg. for inhibition of writhing. In the audiogenic seizure test (Plotnikoff, *J. Pharmacol. Exp. Therap.*, 119, 234, 1957) at an oral dose of 100 mg./kg., it protected 20% of the mice from the convulsions. Activity in these procedures indicates usefulness for the compound as an anti-anxiety (tranquilizer), analgesic, or anticonvulsant agent.

1,2-Dihydro-7-(3-methyl-2-octyl)-9-[2-methyl-4-(piperidino)butyryloxy]-1,4,4-trimethyl-4H-thieno[2,3-c] [1] benzopyran hydrochloride administered orally in a dose of 5 mg./kg., caused an 81% reduction in rat motor activity. At an oral dose of 5 mg./kg., it caused an 82% reduction in methamphetamine-induced hyperactivity in the rat methamphetamine antagonism test. In the rat tail flick test, at an oral dose of 2 mg./kg., it showed significant activity, causing a 47% increase in the pain threshold. Activity in these procedures indicates it has sedative, anti-psychotic, and analgesic activity.

1,2-Dihydro-7-(3-methyl-2-octyl)-9-[4-(piperidino)butyryloxy]-1,4,4-trimethyl-4H-thieno[2,3-c][1]benzopyran administered orally in a dose of 5 mg./kg., caused an 82% reduction in rat motor activity. At an oral dose of 5 mg./kg., it caused a 70% reduction in methamphetamine-induced hyperactivity in the rat methamphetamine antagonism test. In the rat tail flick test (P. D'Armour et al., J. Pharmacol Exper. Therap. 72, 74, 1941),, at an oral dose of 40 mg./kg., it showed significant activity, causing an 84% increase in the pain threshold. At an oral dose of 20 mg./kg., it showed marked activity in the mouse modified DOPA potentiation test. At an oral dose of 10 mg./kg., it caused a 100% reduction in fighting behavior in the mouse fighting test. It has utility as a sedative, anti-psychotic, analgesic, anti-depressant, or anti-anxiety (tranquilizer) agent.

The compounds provided by this invention thus have antidepressant, anti-anxiety, analgesic and anticonvulsant activity although, obviously, specific compounds will generally not have all these activities simultaneously.

The amount of active ingredient administered may be varied; however, it is necessary that the amount of active ingredient be such that a suitable dosage is given. The selected dosage depends upon the desired therapeutic effect, on the route of administration and on the duration of treatment. Dosages of from 0.1 to 25 mg./kg. of body weight daily, preferably in divided doses, i.e., 3 to 4 times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used for form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg. of active agent.

A typical tablet can have the composition:

| | Mg |
|---|---|
| Active agent (1) | 100 |
| Starch U.S.P. | 57 |
| Lactose U.S.P. | 73 |
| Talc. U.S.P. | 9 |
| Stearic acid | 12 |

(1) 1,2-dihydro-4,4-dimethyl-9-[4-(piperidino)butyryloxy]-7-(3-methyl-2-octyl)-4H-thieno-[2,3-c][1]benzopyran hydrochloride.

The compounds of Formula I exhibit both oral and parenteral activity and accordingly can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The following examples are presented to further illustrate the invention.

EXAMPLE 1

1,2-Dihydro-9-hydroxy-7-(3-methyl-2-octyl)-4-oxo 4H-thieno[2,3-c][1]benzopyran

A. Methyl 3-oxo-2,3,4,5-tetrahydrothiophene-2-carboxylate

The procedure of Woodward and Eastman (J. Am. Chem. Soc. 68, 2229 (1946) was followed for the cyclization of 100 g. (0.55 mole) of methyl 3-(methoxycarbonylmethylthio)propionate to give 56 g. (65%) of methyl 3-oxo-2,3,4,5-tetrahydrothiophene-2-carboxylate.

B. 1,2-Dihydro-9-hydroxy-7-(3-methyl-2-octyl)-4-oxo-4H-thieno[2,3-c][1]benzopyran A solution of 2,5 g. (0.011 mole) of 5-(3-methyl-2-octyl)resorcinol and 2.0 g. (0.013 mole) of the methyl 3-oxo2,3,4,5-tetrahydrothiophene-2-carboxylate in 50 ml. of absolute ethanol in a three-necked flask equipped with drying tube was cooled in an ice-water bath and saturated with dry hydrogen chloride. The 5-(3-methyl-2-octyl) resorcinol was prepared according to the method of Adams, MacKenzie and Loewe (J. Am. Chem. Soc. 70, 664–8 (1948). The reaction mixture was allowed to stand for 3 days at room temperature, during which time a heavy yellow solid formed. The hydrogen chloride was evaporated, the mixture was concentrated and the solid was filtered and washed with ethanol. The yield of the crude benzopyrone thus obtained was 2.6 g. (59%), m.p. 190°–205°C.

Repeated crystallization from absolute ethanol gave an analytical sample of the material, m.p. 209-212°C.

Anal. Calcd. for $C_{20}H_{26}O_3S$: C, 69.36; H, 7.51; S, 9.25.

Found: C, 69.15; H, 7.41; S, 9.30.

EXAMPLE 2

1,2-Dihydro-9-hydroxy-7-methyl-4-oxo-4H-thieno[2,3-c][1]benzopyran

Following a procedure similar to that described in Example 1B hereinabove, methyl 3-oxo-2,3,4,5-tetrahydrothiophene-2-carboxylate is reacted with 5-methylresorcinol to give 1,2-dihydro-9-hydroxy-7-methyl-4-oxo-4H-thieno[2,3-c][1]benzopyran.

EXAMPLE 3

1,2-Dihydro-7-(2-heptyl)-9-hydroxy-4-oxo-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(2-heptyl)resorcinol to give 1,2-dihydro-7-(2-hetpyl)-9-hydroxy-4-oxo-4H-thieno [2,3-c][1]benzopyran.

EXAMPLE 4

7-(3-Cyclopropyl-2-propyl)-1,2-dihydro-9-hydroxy-4-oxo-4H-thieno[2,3-c][1]benzopyran Following a procedure similar to that described in Example 1B hereinabove, methyl 3-oxo-2,3,4,5-tetrahydrothiophene-2-carboxylate is reacted with 5-(3-cyclopropyl-2-propyl)resorcinol to give 7-(3-cyclopropyl-2-propyl)-1,2-dihydro-9-hydroxy-4-oxo-4H-thieno[2,3-c][1]benzopyran.

EXAMPLE 5

1,2-Dihydro-9-hydroxy-4-oxo-7-(1-pentyl)-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(1-pentyl)resorcinol to give 1,2-dihydro-9-hydroxy-4-oxo-7-(1-pentyl)-4H-thieno[2,3-c][1]benzopyran.

EXAMPLE 6

7-(1-Cyclohexylethyl)-1,2-dihydro-9-hydroxy-4-oxo-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(1-cyclohexylethyl) resorcinol to give 7-(1-cyclohexylethyl)-1,2-dihydro-9-hydroxy-4-oxo-4H-thieno[2,3-c][1]benzopyran.

EXAMPLE 7

1,2-Dihydro-7-(2-eicosyl)-9-hydroxy-4-oxo-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(2-eicosyl)resorcinol to give 1,2-dihydro-7-(2-eicosyl)-9-hydroxy-4-oxo-4H-thieno [2,3-c][1]benzopyran.

EXAMPLE 8

1,2-Dihydro-4,4-dimethyl-9-hydroxy-7-(3-methyl-2-octyl)-4H-thieno[2,3-c][1]benzopyran The Grignard reagent was prepared by bubbling bromomethane into a mixture of 7.2 g. (0.3 mole) of magnesium turnings in ether. When all the magnesium had reacted, the solution was refluxed for a short time to remove the excess bromomethane. A solution of 9.0 g. (0.026 mole) of 1,2-dihydro-9-hydroxy-7-(3-methyl-2-octyl)-4-oxo-4H-thieno[2,3-c][1]benzopyran in 250 ml. of benzene was added to the methylmagnesium bromide and the reaction mixture was kept at 45° for 24 hours. After the addition of saturated ammonium chloride, the benzene/ether layer was separated, and the aqueous layer was extracted with ether. The combined organic layers were washed with water, dried over sodium sulfate and evaporated to give a greenish, gummy residue. The material was pure by thin layer chromatography (MeOH/CHCL$_3$) and infrared and nuclear magnetic resonance indicated the compound to be 5-(3-methyl-2-octyl)-2-[4,5-dihydro-2-(2-hydroxy-2-propyl)3-yl]resorincol.

2.0 g. of the triol was dissolved in benzene and refluxed for 3 hours in the presence of a small amount of p-toluenesulfonic acid. The benzene solution was concentrated and the residue was chromatographed using magnesium silicate and graded ether/petroleum ether. The infrared, ultraviolet and nuclear magnetic resonance spectra confirmed the structure.

Anal. Calcd. for $C_{22}H_{32}O_2S$: C, 73.33; H, 8.91; S, 8.91. Found: C, 73.10; H, 9.16; S, 8.75.

The gum exhibited $\lambda_{max}^{EtOH}$ 320 m$\mu$ (log $\epsilon$ 3.951). Infrared, ultraviolet and nuclear magnetic resonance spectra confirmed the pyran structure.

EXAMPLE 9

1,2-Dihydro-4,4-dimethyl-9-[4-(morpholino)-butyryloxy]-7-(3-methyl-2-octyl)-4H-thieno[2,3-c][1] benzopyran hydrochloride 1,14 g. (3.17 mmoles) of 1,2-dihydro-4,4-dimethyl9-hydroxy-7-(3-methyl-2-octyl)-4H-thieno[2,3-c] [1]benzopyran (prepared according to the method of Example 8) 0.69 g. (3.35 mmoles) of dicyclohexylcarbodiimide and 0.665 g. (3.17 mmoles) of γ-morpholinobutyric acid hydrochloride (Cruickshank and Sheehan, *J. Am. Chem. Soc.*, 83, 2891 (1961), m.p. 180°–182°C.) were combined in 55 ml. of methylene chloride and stirred at room temperature for 4½ hours. The insoluble dicyclohexylurea was removed by filtration and the methylene chloride was removed on a rotary evaporator. The residue crystallized from 30 ml. of ether and the solid was filtered and recrystallized from benzene/ether to give 0.5 g. (29%) of colorless crystals, m.p. 123°–124°C.

The material showed a R$_f$ of 0.5 in tlc (5% MeOH/CHCL$_3$); the infrared and nuclear magnetic resonance spectra were in agreement with the proposed structure.

Anal. Calcd. for $C_{30}H_{46}ClNO_4S$: C, 65.27; H, 8.40; N, 2.54. Found: C, 64.46; H, 8.19; N, 2.56.

EXAMPLE 10

1,2-Dihydro-4,4-dimethyl-9-[4-(piperidino)butyryloxy]-7-(3-methyl-2-octyl)-4H-thieno[2,3-c][1]benzopyran hydrochloride 2.86 g. (7.95 mmoles) of 1,2-dihydro-4,4-dimethyl-9-hydroxy-7-(3-methyl-2-octyl)-4H-thieno[2,3-c][1]benzopyran, 1.65 g. (7.95 mmoles) of γ-piperidinobutyric acid hydrochloride (Cruickshank and Sheehan, *J. Am. Chem. Soc.* 83, 2891 (1961), m.p. 190°–192°C.) and 1.72 g. (8.35 mmoles) of dicyclohexylcarbodiimide were combined in 150 ml. of methylene chloride and stirred at room temperature for 4 hours. The insoluble by-product of dicyclohexylurea was removed by filtration and the methylene chloride was removed on a rotary evaporator. The residue was dissolved in benzene (30 ml.) and ethyl ether (30 ml.) was added until a colorless solid appeared. The material was filtered and recrystallized from benzene/ether to give 3.2 g. (73%) of colorless crystals, m.p. 165°–167°C.

The material was pure by thin layer chromatography (10% MeOH/CHCl$_3$); the infrared and nuclear magnetic resonance spectra were in agreement with the proposed structure.

Anal. Calcd. for $C_{31}H_{48}ClNO_3S$: C, 67.66; H, 8.79; N, 2.55. Found: C, 67.67; H, 8.88; N, 2.65.

EXAMPLE 11

1,2-Dihydro-9-[3-(piperidino)propionoxy]-4,4,7-trimethyl-4H-thieno[2,3-c][1]benzopyran Following a procedure similar to that described in Example 8 hereinabove, 1,2-dihydro-9-hydroxy-7-methyl-4-oxo-4H-thieno[2,3-c][1]benzopyran is reacted with methyl magnesium bromide to give 1,2-dihydro-9-hydroxy-4,4,7-trimethyl-4H-thieno-[2,3-c][1]benzopyran. The benzopyran is then reacted with β-piperidinopropionic acid and dicyclohexylcarbodiimide to yield the desired ester.

EXAMPLE 12

1,2-Dihydro-4,4-dimethyl-7-(2-heptyl)-9-morpholinoacetoxy-4H-thieno[2,3-c][1]benzopyran By reacting 1,2-dihydro-7-(2-heptyl)-9-hydroxy-4-oxo-4H-thieno[2,3-c][1]benzopyran with methyl magnesium bromide in a procedure similar to that described hereinabove in Example 8, there is obtained 1,2-dihydro-4,4-dimethyl-7-(2-heptyl)-9-hydroxy-4H-thieno[2,3-c][1]benzopyran. The benzopyran is then reacted with morpholinoacetic acid and dicyclohexylcarbodiimide to yield the desired ester.

EXAMPLE 13

7-(3-Cyclopropyl-2-propyl)-4,4-dimethyl-1,2-dihydro-9[4-(piperidino)butyryloxy]-4H-thieno[2,3-c][1]benzopyran hydrochloride 7-(3-cyclopropyl-2-propyl)-1,2-dihydro-9-hydroxy-4-oxo-4H-thieno[2,3-c][1]benzopyran is reacted with methyl magnesium bromide in a procedure similar to that described hereinabove in Example 8 to give 7-(3-cyclopropyl-2-propyl)-4,4-dimethyl-1,2-dihydro-9-hydroxy-4H-thieno[2,3-c][1]benzopyran which is then reacted with γ-piperidinobutyric acid hydrochloride and dicyclohexylcarbodiimide according to the method of Example 10 to yield the desired ester.

EXAMPLE 14

1,2-Dihydro-4,4-dimethyl-9-[5-(N-methylpiperazino)valeryloxy]7-(1-pentyl)-4H-thieno[2,3-c][1]benzopyran dihydrobromide 1,2-Dihydro-9-hydroxy-4-oxo-7-(1-pentyl)-4H-thieno[2,3-c][1]benzopyran is reacted with methyl magnesium bromide in a procedure similar to that described hereinabove in Example 8 to give 1,2-dihydro-4,4-dimethyl-9-hydroxy-7-(1-pentyl)4H-thieno[2,3-c][1]benzopyran. The benzopyran is then reacted with N-methylpiperazinovaleric acid dihydrobromide and dicyclohexylcarbodiimide according to the method of Example 9 to yield the desired ester.

EXAMPLE 15

7-(1-Cyclohexylethyl)-1,2-dihydro-4,4-dimethyl-9-[3-(homopiperidino)propionyloxy]-4H-thieno[2,3-c][1]benzopyran 7-(1-Cyclohexylethyl)-1,2-dihydro-9-hydroxy-4-oxo-4H-thieno[2,3-c][1]benzopyran is reacted with methyl magnesium bromide according to the procedure described hereinabove in Example 8 to give 7-(1-cyclohexylethyl)-1,2-dihydro-4,4-dimethyl-9-hydroxy-4H-thieno[2,3-c][1]benzopyran. The benzopyran is then reacted with β-homopiperidinopropionic acid and dicyclohexylcarbodiimide according to the method of Example 9 to yield the desired ester.

EXAMPLE 16

1,2-Dihydro-4,4-dimethyl-7-(2-eicosyl)-9-[4-(thiomorpholino)butyryloxy]-4H-thieno[2,3-c][1]benzopyran 1,2-Dihydro-7-(2-eicosyl)-9-hydroxy-4-oxo-4H-thieno[2,3-c][1]benzopyran is reacted with methyl magnesium bromide according to the procedure described hereinabove in Example 8 to give 1,2-dihydro-4,4-dimethyl-7-(2-eicosyl)-9-hydroxy-4H-thieno[2,3-c][1]benzopyran. The benzopyran is then reacted with γ-thiomorpholinobutyric acid, acetate salt and dicyclohexylcarbodiimide according to the method of Example 10 to yield the desired ester.

EXAMPLE 17

4,4-di(1-Hexyl)-1,2-dihydro-7-methyl-9-[4-(pyrrolidino)butytyloxy]-4H-thieno[2,3-c][1]benzopyran hydrobromide By reacting 1,2-dihydro-9-hydroxy-7-methyl-4-oxo-4H-thieno[2,3-c][1]benzopyran with n-hexyl magnesium bromide, using the procedure described in Example 8, there is obtained 4,4-di(1-hexyl)-1,2-dihydro-9-hydroxy-7-methyl-4H-thieno [2,3-c][1]benzopyran. The benzopyran is then reacted with γ-pyrrolidinobutyric acid, hydrobromide salt and dicyclohexylcarbodiimide according to the method of Example 10 to yield the desired ester.

EXAMPLE 18

7-(3-cyclopropyl-2-propyl)-4,4-di(1-hexyl)-1,2-dihydro-9-morpholinoacetoxy-4H-thieno-[2,3-c][1]benzopyran By reacting 7-(3-cyclopropyl-2-propyl)-1,2-dihydro-9-hydroxy-4-oxo-4H-thieno[2,3-c][1]benzopyran with n-hexyl magnesium bromide, using the procedure described above in Example 8, there is obtained 7-(3- cyclopropyl-2-propyl)-4,4-di(1-hexyl)-1,2-dihydro-9-hydroxy-4H-thieno[2,3-c] [1]benzopyran. The benzopyran is then reacted with morpholinoacetic acid and dicyclohexylcarbodiimide according to the method of Example 9 to yield the desired ester.

EXAMPLE 19

1,3-Dihydro-4,4-dimethyl-7-(3-methyl-2-octyl)-9-[4-(morpholinobutyryloxy]-4H-thieno[3,4-c] [1]benzopyran hydrochloride

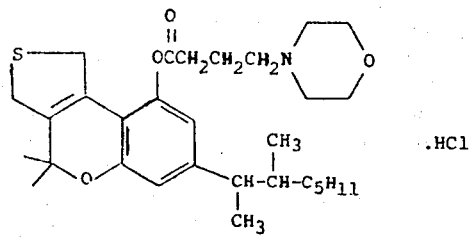

A. Methyl 4-oxo-2,3,4,5-tetrahydrothiophene-3-carboxylate

The procedure of Woodward and Eastman (J. Am. Chem. Soc. 68, 2229 (1946) was followed for the cyclization of 48 g. (0.25 mole) of methyl 3-(methoxycarbonylmethylthio)propionate to give 19.8 g. (50%) methyl 4-oxo-2,3,4,5-tetrahydrothiophene-3-carboxylate. The infrared and nuclear magnetic resonance spectra indicated the product to be the desired isomer.

B. 1,3-Dihydro-9-hydroxy-7-(3-methyl-2-octyl)-4-oxo-4H-thieno[2,3-c] [1]benzopyran A solution of 20 g. (0.125 mole) of methyl-4-oxo-2,3,4,5-tetrahydrothiophene-3-carboxylate and 32 g. (0.135 mole of 5-(3-methyl-2-octyl)resorcinol in 200 ml. of absolute ethanol was cooled in an ice-salt bath and saturated with anhydrous hydrogen chloride. The reaction mixture was allowed to stand at room temperature for 72 hours and the solid which formed was removed by filtration. Recrystallization from ethanol gave 16 g. (37%) m.p. 165°–166°C. The structure was confirmed by infrared and nuclear magnetic resonance spectra.

C. 1,3-Dihydro-4,4-dimethyl-7-(3-methyl-2-octyl)-9-[4-(morpholino)butyryloxy]-4H-thieno[3,4-c] [1]benzopyran hydrochloride A suspension of 6.0 g. (0.017 mole) of the above pyrone in 150 ml. of benzene was added to a Grignard reagent prepared by adding bromomethane to 8.47 g. (0.36 mole) of magnesium turnings in 100 ml. of ether. The mixture was heated at 45°C. for 24 hours and then decomposed by the addition of dilute hydrochloric acid solution. The organic layer was separated, washed with water, dried over sodium sulfate and evaporated to give a gummy residue. This material was dissolved in benzene and refluxed for 3 hours with a few crystals of p-toluenesulfonic acid. The benzene solution was washed, dried and evaporated to give a dark gum which was chromatographed using magnesium silicate (60–100 mesh) and graded ether/petroleum ether solvent mixtures. 2.6 g. (42%) of colorless gum was obtained. The material was pure by thin layer chromatography (20% ether/petroleum ether) and exhibited λ284 mμ (logϵ4.157). The infrared and nuclear magnetic resonance spectra were in agreement with the proposed structure.

Anal. Calcd. for $C_{22}H_{32}O_2S$: C, 73.33; H, 8.91. Found: C, 73.21; H, 8.76.

The benzopyran is reacted with γ-morpholinobutyric acid hydrochloride and dicyclohexylcarbodiimide to obtain the desired product.

EXAMPLE 20

1,2-Dihydro-10-hydroxy-8-(3-methyl-2-octyl)-5-oxo-4H,5H-thiopyrano[3,4-c] [1]benzopyran A solution of 6.4 g. (0.027 mole) of 5-(3-methyl-2-octyl-resorcinol of Example 1 and 5.0 g. (0.0266 mole) of ethyl 4-oxo-2,3,5,6-tetrahydro-4H-thiopyran-3-carboxylate [prepared according to the method of Bennett and Scorah, J. Chem. Soc., 194 (1927)] in 35 ml. of absolute ethanol was cooled in an ice bath while it was saturated with hydrogen chloride. The resulting deep red solution was tightly stoppered and allowed to stand at room temperature for 120 hours. After one day yellow crystalline material had collected on the bottom of the flask. The reaction mixture was warmed gently on the steam bath for 15 minutes, cooled and poured onto a water-ice mixture. The gum-like material that precipitated was extracted with several portions of chloroform. The chloroform solution was washed with aqueous potassium bicarbonate and with water and dried over sodium sulfate. Evaporation of the solvent left 7.5 g. of a light-colored solid. This material was triturated several times with boiling petroleum ether to remove unreacted keto ester. The residue was recrystallized from an ethyl acetate-petroleum ether mixture to give 6.5 g. (68%) of the desired compound, m.p. 153°–155°C.

The nuclear magnetic resonance spectrum of this material was consistent with the assigned structure. From another preparation the analytical sample, m.p. 150°–152°C., was obtained after two recrystallizations from ethyl acetate-petroleum ether. It exhibited $\lambda_{max}^{EtOH}$ 310 mμ (logϵ 3.996).

Anal. Calcd. for $C_{21}H_{28}O_3S$: C, 70.00; H, 7.78; S, 8.89. Found: C, 69.99; H, 7.99; S, 8.83.

EXAMPLE 21

1,2-Dihydro-5,5-dimethyl-10-hydroxy-8-(3-methyl-2-octyl)-4H, 5H-thiopyrano[3,4-c] [1]benzopyran The Grignard reagent was prepared from 8.75 g (0.36 mole) of magnesium shavings in 100 ml. of anhydrous diethyl ether by bubbling in methyl bromide until all of the magnesium had dissolved. Excess methyl bromide was removed by a brief refluxing. A slurry of 10.8 g (0.03 mole) of 1,2-dihydro-10-hydroxy-8-(3-methyl-2-octyl)-5-oxo-4H,5H-thiopyrano[3,4-c] [1]benzopyran in 200 ml of warm diethyl ether was added rapidly to the well-stirred Grignard reagent cooled in ice. After 20 minutes the ice bath was removed, and the solution was allowed to stand at room temperature for 72 hours.

Excess Grignard reagent was destroyed (ice cooling) by the careful addition of 5 ml. of methanol in 5 ml. of diethyl ether, followed by 10 ml. of saturated ammonium chloride and by dilute hydrochloric acid to dissolve all precipitated solids. The ether layer was separated, washed with water and with saturated sodium chloride, dried and concentrated. Dehydration of the triol, thus obtained, and ring closure, was effected by dissolving the oily residue in methanol, adding 10 drops of concentrated hydrochloric acid, and warming the drab green solution in a water bath. The solution was concentrated in a rotary evaporator, to leave 11.1 g. of crude pyran as a green-brown resin.

The product was purified by chromatography on magnesium silicate from which it was eluted with diethyl ether/petroleum ether solvent mixtures. The major fractions were combined to give 7.9 g. (71%) of the 1,2-dihydro-5,5-dimethyl-10-hydroxy-8-(3-methyl-2-octyl)-4H,5H-thiopyrano [3,4-c] [1]benzopyran as a dark green, clear resin that darkened slowly on aging.

The nuclear magnetic resonance and infrared spectra were consistent with the structure of the desired product. The ultraviolet spectrum showed $\lambda_{max}^{EtOH}$ 275 m$\mu$ (log$\epsilon$ 3.6).

Anal. Calcd. for $C_{23}H_{34}O_2S$: C, 73.74; H, 9.15; S, 8.56. Found: C, 73.57; H, 9.14; S, 8.76.

EXAMPLE 22

1,2-Dihydro-5,5-dimethyl-8-(3-methyl-2-octyl)-10-[4-(piperidino)butyryloxy]-4H,5H-thiopyrano[3,4-c][1]benzopyran hydrochloride The benzopyran of Example 21 is reacted with γ-piperidinobutyric acid hydrochloride and dicyclohexylcarbodiimide according to the method of Example 9 to yield the desired ester.

EXAMPLE 23

Methyl 3-oxo-2,3,4,5-tetrahydro-6H-thiopyran-2-carboxylate

The procedure of Leonard and Figueras (*J. Am. Chem. Soc.* 74, 917 (1952)) was followed for the cyclization of 20 g. of carbmethoxymethyl γ-carbmethoxypropyl sulfide to give 11.1 g. (70%) of methyl 3-oxo-2,3,4,5-tetrahydro-6H-thiopyran-2-carboxylate. The structure was confirmed by infrared and nuclear magnetic resonance spectra.

EXAMPLE 24

1,2-Dihydro-10-hydroxy-8-(3-methyl-2-octyl)-5-oxo-3H,5H-thiopyrano[2,3-c][1]benzopyran A solution of 14.2 g. (0.06 mole) of 5-(3-methyl-2-octyl)resorcinol and 11.1 g. (0.063 mole) of methyl-3-oxo-2,3,4,5-tetrahydro-6H-thiopyran-2-carboxylate in 90 ml. of absolute ethanol was cooled in an ice-salt bath and saturated with anhydrous hydrogen chloride. After standing for 2 days at room temperature, the ethanol was removed on a rotary evaporator. The residue was dissolved in ether, washed with sodium bicarbonate solution and dried over sodium sulfate. Evaporation of the solvent gave 28.0 g. of residue which was chromatographed using magnesium silicate (60–100 mesh) and graded methanol/chloroform solvent mixtures. A total of 10 g. of crude solid was obtained from the 1% methanol/chloroform fractions. The material was recrystallized twice from ethyl acetate/hexane to give 8.5 g. 40%) of colorless crystals, m.p. 131°–133°C. The proposed structure was confirmed by infrared and nuclear magnetic resonance spectra.

EXAMPLE 25

1,2-Dihydro-5,5-dimethyl-10-hydroxy-8-(3-methyl-2-octyl)-3H,5H-thiopyrano[2,3-c][1]benzopyran Methyl magnesium bromide was prepared by bubbling bromomethane into a mixture of 7.68 g. (0.32 mole) of magnesium turnings in ether. When all the magnesium had reacted, the solution was refluxed for a short time to remove the excess bromoethane. A solution of 6.96 g. (0.02 mole) of the pyrone (prepared as above) in benzene was added and the reaction mixture was kept at 45°C. for 24 hours. The reaction mixture was decomposed with saturated ammonium chloride, the organic layer was separated and the aqueous layer was extracted twice with ether. The organic layers were combined, washed with water, dried and evaporated to give a gummy residue. The infrared and nuclear magnetic resonance spectra indicated the compound to be 5-(3-methyl-2-octyl)-2-[4,5-dihydro-2-(2-hydroxy-2-propyl)-6-H-thiopyran-3-yl]resorcinol.

A small quantity of p-toluenesulfonic acid was added to a benzene solution of the above triol and the mixture was heated at relfux for 1½ hours in the presence of nitrogen. The benzene solution was washed with sodium bicarbonate solution, dried over sodium sulfate and evaporated to give a greenish-brown residue. Chromatography using magnesium silicate (60–100 mesh) and graded ether/petroleum ether solvent mixtures gave 5.2 g. (60%) of a nearly colorless gum. The gum exhibited $\lambda_{max}^{EtOH}$ 305 m$\mu$ (log$\epsilon$ 4.262) and the infrared, nuclear magnetic resonance and ultraviolet spectra confirmed the structure as 1,2-dihydro-5,5-dimethyl-10-hydroxy-8-(3-methyl-2-octyl)-3H,5H-thiopyrano[2,3-c][1]benzopyran.

Anal. Calcd. for $C_{23}H_{34}O_2S$: C, 73.73; H, 9.15; S, 8.54. Found: C, 73.55; H, 9.12; S, 8.45.

EXAMPLE 26

1,2-Dihydro-5,5-dimethyl-8-(3-methyl-2-octyl)-10-[4-(morpholino)butyryloxy]-3H,5H-thiopyrano[2,3-c][1]benzopyran hydrochloride The benzopyran of Example 25 is reacted with γ-morpholinobutyric acid, hydrochloride salt and dicyclohexylcarbodiimide according to the method of Example 10 to yield the desired ester.

EXAMPLE 27

1,2-Dihydro-5,5-dimethyl-8-(3-methyl-2-octyl)-10-[4-(piperidino)butyryloxy]-3H,5H-thiopyrano[2,3-c][1]benzopyran hydrochloride

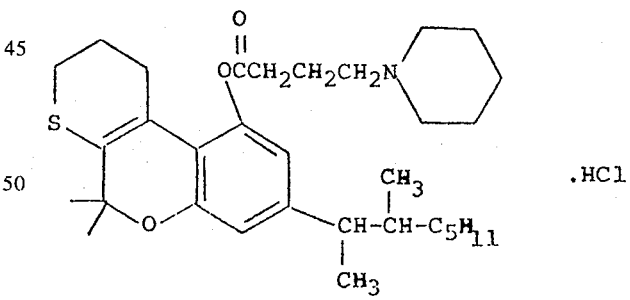

1.5 g (4.0 mmole) of 1,2-dihydro-5,5-dimethyl-10-hydroxy-8-(3-methyl-2-octyl)-3H,5H-thiopyrano[2,3-c][1]benzopyran was combined with 0.83 g (4.0 mmole) of γpiperidinobutyric acid hydrochloride, 0.88 g. (4.25 mmole) of dicyclohexylcarbodiimide and 75 ml. of methylene chloride and stirred at room temperature for 6 hours. The reaction mixture was cooled, and the byproduct of dicyclohexylurea was removed by suction filtration. The mother liquor was evaporated to give a foamy residue which crystallized from 25 ml. of cyclohexane. The solid was filtered and dried to give 1.8 g. (80% yield) of colorless crystals, m.p. 136°–138°C. The material was pure by thin layer chromatography (10% MeOH/CHCl₃) and the infrared and nuclear magnetic resonance spectra were consistent with the proposed structure.

Anal. Calcd. for $C_{32}H_{50}ClNO_3S$ (MW = 564.18): C, 68.12; H, 8.93; N, 2.48; Found: C, 67.93; H, 9.05; N, 2.50.

EXAMPLE 28

1,2-Dihydro-5,5-dimethyl-8-(3-methyl-2-octyl)-10-[2-methyl-4-(piperidino)butyryloxy]-3H,5H-thiopyrano[2,3-c][1]benzopyran hydrochloride

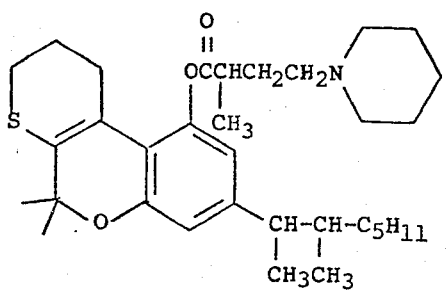

A combination of 0.5 g. (1.33 mmole) of 1,2-dihydro-5,5-dimethyl-10-hydroxy-8-(3-methyl-2-octyl)-3H,5H-thiopyrano [2,3-c][1]-benzopyran, 0.30 g. (1.45 mmole) of dicyclohexylcarbodiimide, 0.29 g (1.33 mmole) of 2-methyl-4-piperidinobutyric acid hydrochloride and 25 ml. of methylene chloride was stirred at room temperature for 16 hours. The reaction mixture was cooled for several hours and the byproduct of dicyclohexylurea was removed by filtration. After removal of the solvent on a rotary evaporator, the residue was combined with 15 ml. of diethyl ether and an additional amount of the dicyclohexylurea was removed by filtration. The solvent was evaporated and the residue thoroughly dried to give 0.40 g (50%) of beige solid. The sample was pure by thin layer chromatography (10% MeOH/CHCl₃), and the infrared spectrum was consistent with the desired product. Anal. Calcd. for $C_{33}H_{52}ClNO_3S\cdot H_2O$ (MW=596.28) C, 66.44; H, 9.13; N, 2.35; Found: C, 65.84; H, 9.01; N, 2.70.

The 2-methyl-4-piperidinobutyric acid hydrochloride used in this example can be prepared as follows:

A. Ethyl 4-Bromo-2-methylbutyrate

The method of Lee V. Phillips in U.S. Pat. No. 3,299,100 was used to prepare α-methyl-γ-butyrolatone and this material was converted to ethyl 4-bromo-2-methylbutyrate via the procedure of G. Jones and J. Wood, "The Synthesis of 9-Azasteroids-II", *Tetrahedron*, 21 2961 (1965).

B. Ethyl-2-methyl-4-piperidinobutyrate 10.5 g. (0.05 mole) of ethyl 4-bromo-2-methylbutyrate was combined with 17.0 g. (0.20 mole) of piperidine and 100 ml. of benzene and stirred for 16 hours at room temperature and then heated at 60°C. for 4 hours. The reaction mixture was cooled and the colorless solid which appeared was removed by filtration. The mother liquor was concentrated to give a mobile yellow liquid which distilled (b.p. 78°C. at 0.25 mm) as 6.7 g. (63%) of colorless liquid.

C. 2-Methyl-4-piperidinobutyric acid hydrochloride 6.5 g. (0.030 mole) of ethyl 2-methyl-4-piperidinobutyrate was combined with a mixture of 45 ml. of water and 45 ml. of concentrated hydrochloric acid and heated at reflux for 16 hours. The solution was concentrated under reduced pressure (water aspirator) to give a residue which crystallized upon addition of 50 ml. of diethyl ether. The ether was decanted, and the solid was triturated with acetone and filtered. Recrystallization from acetic acid/acetone gave 3.38 g. of colorless crystals, m.p. 166°–168°C. and a second crop of 1.27 g. of solid, m.p. 165°–168°C. The total yield for both batches was 69%.

Anal. Calcd. for $C_{10}H_{20}ClNO_2$ (MW = 221.72): C, 54.20; H, 9.09; N, 6.32. Found: C, 54.17; H, 9.15; N, 6.36.

EXAMPLE 29

1,2-Dihydro-7-(3-methyl-2-octyl)-9-[2-methyl-4-(piperidino)butyryloxy]-1,4,4-trimethyl-4H-thieno[2,3-c][1]benzopyran hydrochloride

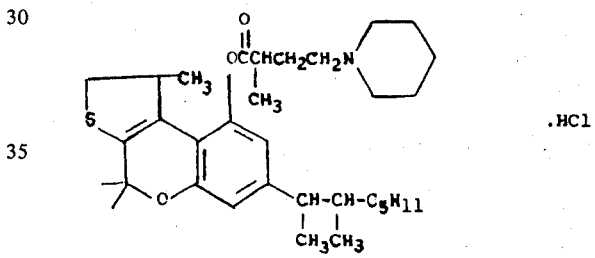

2.16 g. (5.75 mmole) of 1,2-dihydro-9-hydroxy-7-(3-methyl-2-octyl)-1,4,4-trimethyl-4H-thieno[2,3-c][1] benzopyran was combined with 1.27 g. (5.75 mmole) of 2-methyl-4-piperidinobutyric acid hydrochloride, 1.25 g. (6.07 mmole) of dicyclohexylcarbodiimide and 110 ml. of methylene chloride and stirred at room temperature for 18 hours. The reaction mixture was cooled, and the by-product of dicyclohexylurea was removed by filtration. The solvent was removed on a rotary evaporator to give a foamy residue which was dissolved in 50 ml. of diethyl ether. An additional quantity of colorless solid appeared and it was also removed by filtration. The diethyl ether was removed and the resulting residue was thoroughly dried to give 2.70 g. (81%) of a colorless solid. The sample was pure by thin layer chromatography (10% MeOH/CHCl₃) and the infrared and nuclear magnetic resonance spectra were consistent with the proposed structure.

Anal. Calcd. for $C_{33}H_{52}ClNO_3S$ (MW=578.27) C, 68.54; H, 9.06; N, 2.42; Found C, 68.48; H, 9.11; N, 2.43

The 1,2-dihydro-1,4,4-trimethyl-9-hydroxy-7-(3-methyl-2-octyl)-4H-thieno[2,3-c][1]benzopyran used in the above preparation can be made as subsequently described.

A solution in dry benzene of equimolar amounts of methyl 4-methyl-3-oo-tetrahydrothiophene-2-carboxylate and 5-(3-methyl-2-octyl)resorcinol plus phosphorous oxychloride (5 ml. of benzeneg. of the resorcinol) was warmed for 13 days at 35°–37°C. in an oil bath. Most of the benzene and HCl were removed at reduced pressure, and the dark tarry residue was stirred with ether and water until solution was complete. The ether layer was washed successively with dilute solutions of sodium bicarbonate, sodium hydroxide and sodium carbonate, then with water and saturated sodium chloride. Drying and concentrating the final organic solution left a friable brick-red foamy solid.

The pyrone was recovered from this crude product by chromatography on a magnesium silicate column using 100% $CHCl_3$ and 1:99 $MeOH/CHCl_3$ solvent systems. Fractions containing the desired material were concentrated to dryness and caused to solidify by standing under petroleum ether. The compound was further purified to give a yellow solid, m.p. 105°–107°C., (41% yield).

A solution of 4.6 g. (0.0128 mole) of 1,2-dihydro-9-hydroxy-1-methyl-7-(3-methyl-2-octyl)-4-oxo-4H-thieno[2,3-c][1]benzopyran in 140 ml. of anhydrous diethyl ether was added during 30 min. with stirring to a solution of methylmagnesium bromide in 140 ml. of anhydrous ether, prepared from 3.7 g. (0.154 mole) of magnesium shavings by bubbling in methyl bromide until the solid metal had dissolved. After 15 min. of additional stirring at room temperature, the reaction mixture was heated at reflux for 1.5 hr.

The excess Grignard reagent was decomposed by the addition of a saturated solution of ammonium sulfate followed by additional water and dilute hydrochloric acid. The organic layer was separated, washed to neutrality with water, dried, and evaporated in a rotary evaporator. The residue was dissolved in 30 ml. of warm methanol and was dehydrated by the addition of 2 drops of concentrated hydrochloroic acid and warming. The reaction mixture was added to water and the product was extracted into ethyl ether. The ether solution was washed free of acid, dried, and concentrated in a rotary evaporator, leaving 5.2 g. of a brown oil.

The oil was purified by column chromatography (silica gel, graded ethyl ether/petroleum ether), yielding 4.3 g. (90%) of product as a cloudy, pale yellow oil from the fractions eluted by 1:99 and 2:98 ethyl ether/petroleum ether. The material showed a single spot on thin layer chromatography (silica gel, 1:4 ethyl acetate/hexane) and the nuclear magnetic reasonance and infrared spectra agreed with the assigned structure for 1,2-dihydro-1,4,4-trimethyl-9-hydroxy-7-(3-methyl-2-octyl)-4H-thieno-[2,3-c][1]benzopyran.

Anal. Calcd. for $C_{23}H_{34}O_2S$ (MW = 374.6) C, 73.74; H, 9.15; S, 8.56. Found: C, 73.64; H, 9.15; S, 8.51.

EXAMPLE 30

1,2-Dihydro-2,4,4-trimethyl-9-[4-(morpholino)-butyryloxy]-7-(3-methyl-2-octyl)-4H-thieno[2,3-c][1]benzopyran hydrochloride 1,2-Dihydro-2,4,4-trimethyl-9-hydroxy-7-(3-methyl-2-octyl)-4H-thieno-[2,3-c][1]benzopyran,, dicyclohexylcarbodiimide and γ-morpholinobutyric acid hydrochloride are combined in methylene chloride and stirred at room temperature. The insoluble dicyclohexylurea is removed by filtration and the methylene chloride is removed on a rotary evaporator. The residue is crystallized from ether to give 1,2-dihydro-2,4,4-trimethyl-9-[4-(morpholino)butyryloxy]-7-(3-methyl-2-octyl)-4H-thiemo[2,3-c][1]benzopyran hydrochloride.

The 1,2-dihydro-2,4,4-trimethyl-9-hydroxy-7-(3-methyl-2-octyl)-4H-thieno-[2,3-c][1]benzopyran used as the starting material in the above example can be prepared as follows:

A. Diethyl 4-methyl-3-thiahexanedioate

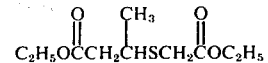

To 250 ml. of ethanol was added 2 g. of sodium followed by the addition of 117 g. of ethyl mercaptoacetate and then 100 g. of ethyl methylacrylate. The mixture was refluxed 17 hours, cooled and 500 ml. of ether added. The reaction mixture was extracted with water and then twice with aqueous sodium bicarbonate solution. The etheral solution was dried over magnesium sulfate and then distilled to give 139 g. of diethyl 4-methyl-3-thiahexanedioate, b.p. 90°–95°C/0.5 mm.

B. Ethyl 5-methyl-3-oxo-tetrahydrothiophene-2-carboxylate

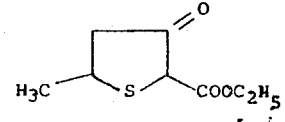

Diethyl 4-methyl-3-thiahexanedioate was converted to ethyl 5-methyl-3-oxo-tetrahydrothiophene-2-carboxylate by reaction with potassium tertiary butoxide in ether in an ice bath. Acetic acid and water are added and then the product was extracted with ether. The crude product (27 g.) had a boiling point of 70°–75°C./0.3 mm.

C. 1,2-Dihydro-9-hydroxy-2-methyl-7-(3-methyl-2-octyl)-4-oxo-4H-thieno-[2,3-c][1]benzopyran

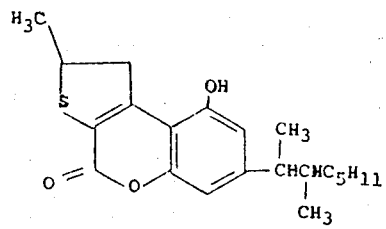

To 45 ml. of ethanol is added 8.8 g. of ethyl 5-methyl-3-oxo-tetrahydrothiophene-2-carboxylate and 5 g. of 5-(3-methyl-2-octyl)resorcinol. The mixture is cooled in ice and hydrogen chloride is bubbled in for one-half hour. The mixture is stoppered and let stand at room temperature for 3 days. The reaction mixture is concentrated and dissolved in ether. The ether solution is extracted twice with water and once with aqueous sodium bicarbonate solution. The solution is dried over magnesium sulfate and concentrated. The 1,2-dihydro-9-hydroxy-2-methyl-7-(3-methyl-2-octyl)-4-oxo-4H-thieno-[2,3-c][1]benzopyran is crystallized from acetonitrile to give 4.65 g., m.p. 146°–149°C.

Anal. Calcd. for $C_{21}H_{28}O_3S$ (MW = 360.6) C, 69.97; H, 7.83. Found: C, 69.89; H, 8.03.

1,2-Dihydro-9-hydroxy-2-methyl-7-(3-methyl-2-octyl)-4-oxo-4H-thieno-[2,3-c][1]benzopyran is reacted in a manner similar to that set forth in Example 8 to give 1,2-dihydro-2,4,4-trimethyl-9-hydroxy-7-(3- methyl-2-octyl)-4H-thieno-[2,3-c][1]benzopyran in 81% yield as a yellow oil.

Anal. Calcd. for: $C_{23}H_{34}O_2S$ (MW = 374.6) C, 73.76; H, 9.15; S, 8.54. Found: C, 74.09; H, 9.68; S, 8.25.

EXAMPLE 31

1,2-Dihydro-7-(3-methyl-2-octyl)-9-[4-(pyrrolidino)-butyryloxy 2,2,4,4-tetramethyl-4H-thieno-[2,3-c][1]benzopyran hydrobromide By reacting 1,2-dihydro-9-hydroxy-7-(3-methyl-2-octyl)-2,2,4,4-tetramethyl-4H-thieno-[2,3-c][1]benzopyran with γ-pyrrolidinobutyric acid hydrobromide salt and dicyclohexylcarbodiimide according to the method of Example 10 there is obained obtained -dihydro-7-(3-methyl-2-octyl)-9-[4-(pyrrolidino)butyryloxy]-2,2,4,4-tetramethyl-4H-thieno-[2,3-c][1]benzopyran hydrobromide.

The 1,2-dihydro-9-hydroxy-7-(3-methyl-2-octyl)-2,2,4,4-tetramethyl-4H-thieno-[2,3-c][1]benzopyran used in this example can be produced as follows:

A. Diethyl 4,4-dimethyl-3-thiahexanedioate

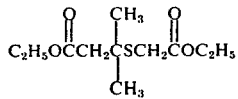

A mixture of 85 grams of ethyl dimethylacrylate, 88 g. of ethyl mercaptoacetate, 185 ml. of ethanol, and sodium ethoxide prepared from 1.6 g. of sodium, was refluxed 16 hrs., cooled and 500 ml. of ether was added. The reaction mixture was extracted with dilute aqueous sodium chloride and hydrochloric acid and then twice with aqueous sodium bicarbonate solution. The reaction mixture was dried over magnesium sulfate and then distilled to give 128 g. of diethyl 4,4-dimethyl-3-thiahexanedioate, b.p. 90°–95°C./0.5 mm.

B. Ethyl 5,5-dimethyl-3-oxo-tetrahydrothiophene-2-carboxylate

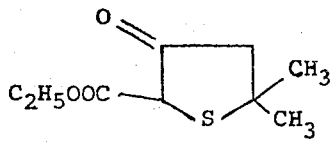

To a stirred suspension of 60 g. of potassium tertiary butoxide in 250 ml. of ether is added dropwise 100 g. of diethyl 4,4-dimethyl-3-thiahexanedioate in 100 ml. of ether over a one hour period while cooling in an ice bath. The mixture is stirred additionally 1 hour in the ice bath and then 35 g. of acetic acid and 150 ml. of water are added. The mixture is extracted with ether and dried over magnesium sulfate. By distillation 60.4 g. of product is obtained, b.p. 70°–75°C./0.5 mm.

C. 1,2-Dihydro-2,2-dimethyl-9-hydroxy-7-(3-methyl-2-octyl)-4-oxo-4H-thieno-[2,3-c][1]benzopyran

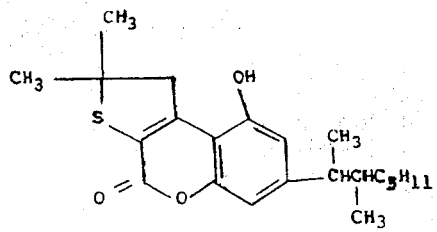

To 100 ml. of ethanol is added 6.2 g. of 5-(3-methyl-2-octyl)resorcinol and 6.2 g. of ethyl 5,5-dimethyl-3-oxo-tetrahydrothiophene-2-carboxylate. The mixture is cooled in ice and hydrogen chloride is bubbled in for one-half hour. The mixture is stoppered and held at room temperature for 3 days. It is then concentrated and ether added, extracted with water and then washed with dilute aqueous sodium bicarbonate solution. The etheral solution is dried over magnesium sulfate and concentrated. The 1,2-dihydro-2,2-dimethyl-9-hydroxy-7-(3-methy-2-octyl)4-oxo-4H-thieno-[2,3-c][1]benzopyran is crystallized from acetonitrile to give 5.0 g., m.p. 155°–163°C.

Anal. Calcd. for: $C_{22}H_{30}O_3S$ (MW = 374.59) C, 70.56; H, 8.08; S, 8.54, Found: C, 70.06; H, 8.15; S, 8.87.

To a solution of methyl magnesium bromide (from 10 g. of Mg) in 150 ml. of ether is added 10 g. of 1,2-dihydro-2 2-dimethyl-9-hydroxy-7-(3-methyl-2-octyl)-4-oxo-4H-thiono-[2,3-c][1]benzopyran in 100 ml. of benzene and 25 ml. of ether. The mixture is stirred overnight at 45°C. The reaction mixture is then treated with saturated ammonium chloride solution. The product is treated with 50 mg. of p-toluenesulfonic acid in 250 ml. of benzene and refluxed for 3 hours. The reaction mixture is shaken with sodium bicarbonate solution and dried over magnesium sulfate. The mixture is concentrated and chromatographed over activated magnesium silicate and eluted with 5% ethyl ether in petroleum ether. The 1,2-dihydro-9-hydroxy-7-(3-methyl-2-octyl)-2,2,4,4-tetramethyl-4H-thieno-[2,3-c][1]benzopyran is obtained as 7.85 g. of a yellow oil.

Anal. Calcd. for: $C_{24}H_{36}O_2S$ (MW = 388.61) C, 74.19; H, 9.34 Found: C, 73.94; H, 9.73

EXAMPLE 32

1,2-Dihydro-7-(3-methyl-2-octyl)-9-[4-(piperidino) butyryloxy]-1,4,4-trimethyl-4H-thieno[2,3-c][1) benzopyran

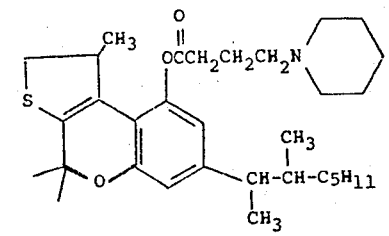

A combination of 2.4 g. (6.4 mmole) of 1,2-dihydro-9-hydroxy-7-(3-methyl-2-octyl)-1,4,4,-trimethyl-4H-thieno[2,3-c][1]benzopyran, 1.33 g. (6.4 mmole) of γ-piperidinobutyric acid hydrochloride, 1.40 g. (6.75 mmole) of dicyclohexylcarbodiimide and 125 ml. of methylene chloride was stirred at room temperature for 18 hours. The reaction mixture was cooled and the byproduct of dicyclohexylurea was removed by filtration. The methylene chloride was distilled off on a rotary evaporator to give a colorless, foamy residue, which was purified on 80 g. of magnesium silicate (60–100 mesh) using a graded methanol/chloroform solvent system. The fractions were monitored by thin layer chromatography, and the appropriate fractions were combined to give 1.23 g. (37%) of the desired material as a golden gum. The infrared and nuclear magnetic resonance spectra were in agreement with the desired product.

Anal. Calcd. for $C_{32}H_{49}NO_3S$ (MW = 527.7). C, 72.82; H, 9.36; N, 2.65; Found: C, 72.88, H, 9.40; N, 2.58.

EXAMPLE 33

1,2-Dihydro-8-(3-methyl-2-octyl)-10-[2-methyl-4-(piperidino)butyryloxy]-1,5,5-trimethyl-3H,5H-thiopyrano[2,3-c][1]benzopyran hydrochloride

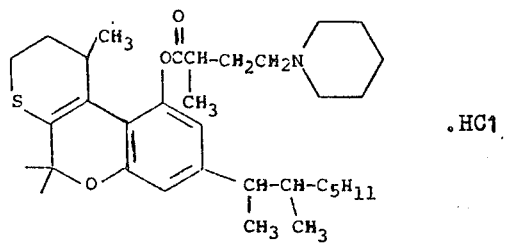

A. Methyl 4-bromo-2-methylbutyrate

Methyl 4-bromo-2-methylbutyrate was obtained in 65% yield by reaction of methanolic hydrogen bromide with 2-methyl-4-butyrolactone in a procedure used by Jones and Wood, Tetrahedron, 21, 2966 (1965) for making the ethyl ester of the bromo acid. The product was a colorless, mobile liquid, b.p. 85°–90°C./15 mm.

B. Methyl 4-(methoxycarbonylmethylthio)-2-methyl butyrate

Methyl 4-(methoxycarbonylmethylthio)-2-methylbutyrate was obtained in 79% yield by reacting methyl 4-bromo-2-methylbutyrate with methyl mercaptoacetate and sodium methoxide in methanol solution, according to a procedure used by Baas, et al., Tetrahedron, 22, 285 (1966). The ester was a colorless liquid, b.p. 92°–95°C./0.1 mm.

C. Methyl 4-methyl-3-oxotetrahydrothiopyran-2-carboxylate

Methyl 4-methyl-3-oxotetrahydrothiopyran-2-carboxylate was obtained in 50% yield from methyl 4-(methoxycarbonylmethylthio)-2-methylbutyrate in a slight modification of the method described by Baas, et al., Tetrahedron, 22, 285 (1966). Our procedure substituted sodium methoxide and toluene for the sodium hydride and benzene used by Baas, et al. The keto ester was a viscous yellow liquid, b.p. 75°–85°c,10.1 mm, which appeared to be a 1:1 mixture of the keto and enol tautomers.

D. 1,2-Dihydro-10-hydroxy-1-methyl-8-(3-methyl-2-octyl)-5-oxo-3H,5H-thiopyrano[2,3-c][1]benzopyran A solution of 4.14 g. (0.022 mole) of methyl 4-methyl-3-oxotetrahydrothiopyran-2-carboxylate and 4.72 g. (0.02 mole) of 5-(3-methyl-2-octyl)resorcinol in 20 ml. of anhydrous ethanol was saturated with dry halogen chloride at ice temperature. After standing at room temperature for 9 days, the reaction mixture was concentrated in a rotary evaporator, and the dark residue was dissolved in benzene.

Much of the unreacted starting material was extracted into 5% sodium hydroxide, and the benzene layer was washed with water and with sodium chloride and then dried and concentrated. The residue (3.52 g.) of crude pyrone was a dark brown liquid which was purified by repeated column chromatography on magnesium silicate using graded diethyl ether/petroleum ether and 100% chloroform as eluants. The desired pyrone was obtained from the fractions eluted with 35:65 ethyl ether/petroleum ether and by trichloromethane. Fractions containing the best quality pyrone were combined to give 1.06 g. (14%) of 1,2-dihydro-10-hydroxy-1-methyl-8-(3-methyl-2-octyl)-5-oxo-3H,5H-thiopyrano[2,3-c][1]benzopyran as a dark amber resin.

E. 1,2-Dihydro-10-hydroxy-8-(3-methyl-2-octyl)-1,5,5-trimethyl-3H,5H-thiopyrano[2,3-c][1]benzopyran A solution of 2.1 g. (0.0056 mole) of 1,2-dihydro-10-hydroxy-1-methyl-8-(3-methyl-2-octyl)-5-oxo-3H,5H-thiopyrano[2,3-c][1]benzopyran in 20 ml. of anhydrous diethyl ether was added to an ice-cold well-stirred solution of the Grignard reagent made from bubbling methyl bromide through a mixture of 1.4 g. (0.057 mole) of magnesium shavings and 60 ml. of anhydrous diethyl ether. The ice bath was removed, and the reaction was allowed to proceed at room temperature for 15 min. as the yellow color faded. The reaction mixture was then heated at reflux for 1.5 hr.

Excess Grignard reagent was decomposed by the addition of a solution of methanol in diethyl ether, and the reaction mixture was poured into 50 ml. of a cold saturated ammonium chloride solution. The clear aqueous layer was extracted with diethyl ether. The combined ether layers were washed, dried, and concentrated. The residual greenish oil was dissolved in methanol, and dehydration of the triol to the pyran was effected by the addition of 3 drops of concentrated hydrochloric acid followed by heating for 5 min. in a hot water bath. Solvent was removed, the residual dark red oil was taken up in diethyl ether, and the solution was washed with water, dried, and concentrated to leave 2.15 g. of a yellow-black oil. The pyran was obtained from this oil by column chromatography on magnesium silicate. Those fractions eluted with 1:99 and 2:98 diethyl ether/petroleum ether were combined to give 1.20 g (55%) of a very viscous, pale yellow syrup, which slowly darkened on aging.

Anal. Calcd. for $C_{24}H_{36}O_2S$: C, 74.18; H, 9.33; S, 8.25. Found: C, 73.96; H, 9.47; S, 8.08.

F. 1,2-Dihydro-8-(3-methyl-2-octyl)-10-[2-methyl-4-(piperidino)butyryloxy]-1,5,5-trimethyl-3H,5H-thiopyrano[2,3-c][1] benzopyran hydrochloride 1,2-dihydro-10-hydroxy-8-(3-methyl-2-octyl)-1,5,5-trimethyl-3H,5H-thiopyrano[2,3-c][1]benzopyran is reacted with 2-methyl-4-piperidinobutyric acid hydrochloride in methylene chloride in the presence of dicyclohexylcarbodiimide, according to the procedure of Example 28, to produce the desired ester.

EXAMPLE 34

1,3-Dihydro-4,4-dimethyl-7-(3-methyl-2-octyl)-9-[2,2-dimethyl-4-(piperidino)butyryloxy]-4H-thieno[3,4-c][1] benzopyran hydrochloride 2,2-Dimethyl-4-piperidinobutyric acid hydrochloride is reacted with 1,3-dihydro-4,4-dimethyl-7-(3-methyl-2-octyl)-9-hydroxy-4H-thieno[3,4-c][1]benzopyran in methylene chloride in the presence of dicyclohexylcarbodiimide to produce 1,3-dihydro-4,4-dimethyl-7-(3-methyl-2-octyl)-9[2,2-dimethyl-4-(piperidino)-butyryloxy]-4H-thieno[3,4-c][1] benzopyran hydrochloride.

The 2,2-dimethyl-4-piperidinobutyric acid hydrochloride used in the process is produced as subsequently described.

The method of Baas et al. in *Tetrahedron*, 22, 288 (1966) was used to convert γ-butyrolactone to 2,2-dimethyl-4-butyrolactone in 45% yield.

A procedure similar to that of Jones and Wood in *Tetrahedron*, 21, 2961 (1965) was used for the preparation of ethyl 2,2-dimethyl-4-bromobutyrate. To a cooled (0°–10°C.) solution of 16.5 g. (0.145 mole) of 2,2-dimethyl-4-butyrolactone in 70 ml. of anhydrous ethanol was added anhydrous hydrogen bromide. Care was taken to keep the temperature at 0°–10°C., and the addition was continued for 2.5 hrs. After standing at room temperature for 24 hrs., the reaction mixture was again cooled and hydrogen bromide was bubbled in for an additional one hour. After standing 48 hrs. at room temperature, the reaction mixture was added to 80 g. of ice. The aqueous layer was separated and extracted three times with ether, and the organic layers were combined, washed twice with 5% sodium bicarbonate solution and water. The solution was dried over sodium sulfate, evaporated, and distilled to give 25.2 g. (78%) of colorless liquid, b.p. 83°–85°C. (10 mm.). The sample was 95% pure.

An aliquot of this sample was converted to the piperidino derivative and subsequently hydrolyzed using methods similar to those described by Blicke et al. in *J. Am. Chem. Soc.*, 63, 2488 (1941).

A mixture of 10.0 g. (0.045 mole) of ethyl 2,2-dimethyl-4-bromobutyrate, 15.3 g. (0.18 mole) of piperidine and 125 ml. of benzene was heated at 60°–70°C. for a total of 4 hrs. and allowed to stand at room temperature for 3 days. The reaction mixture was cooled and filtered to remove the amine hydrobromide which had precipitated. The mother liquor was concentrated, distilled and four fractions were collected. The first three fractions contained various quantities of the unreacted bromo compound. Fraction 4 (3.60 g.) was pure.

3.3 g. (14.5 mmole) of ethyl 2,2-dimethyl-4-piperidinobutyrate was combined with 25 ml. of concentrated hydrochloric acid and 25 ml. of water and stirred at reflux for 18 hrs. The reaction mixture was evaporated under reduced pressure to give a semi-solid residue which crystallized upon trituration with 30 ml. of acetone. The solid was filtered, washed with diethyl ether, and dried under vacuum over potassium hydroxide to give 2.25 g. (66%) of colorless crystals, m.p. 232°–234°C.

Anal. Calcd. for $C_{11}H_{22}ClNO_3$ (MW = 235.75): C, 56.00; H, 9.36; N, 5.96; Found: C, 56.04; H, 9.41; N, 5.94.

The foregoing detailed description has been given for cleaness of understanding only, and no unnecessary limitations should be understood therefrom, as modifications will be obvious to those skilled in the art.

What is claimed is:

1. A compound of the formula

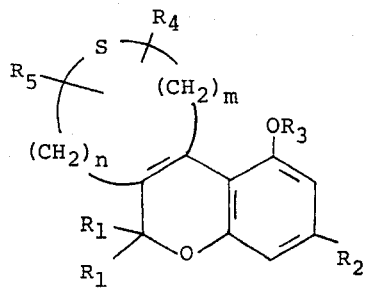

wherein $n$ is 0 to 3, and $m$ is 0 to 3 and $m + n = 2$ or 3, $R_1$ is a lower alkyl having 1 to 6 carbon atoms, $R_2$ is an alkyl having 1 to 20 carbon atoms or cycloalkyl-loweralkyl in which the cycloalkyl group has 3 to 8 carbon atoms and the lower alkyl group has 1 to 6 carbon atoms, $R_4$ is hydrogen or a lower alkyl having 1 to 6 carbon atoms, $R_5$ is hydrogen or a lower alkyl having 1 to 6 carbon atoms, and $R_3$ is

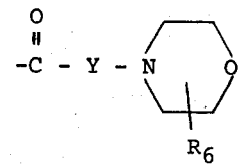

wherein Y is a straight or branched chain $C_1$ to $C_8$ alkylene, $R_6$ is hydrogen or a lower alkyl having 1 to 6 carbon atoms, and the nontoxic acid addition salts thereof.

2. A compound in accordance with claim 1 wherein for $R_3$, Y contains three or four carbons.

3. A compound in accordance with claim 1 wherein $m$ is 1, $n$ is 1 and said compound is represented by the formula

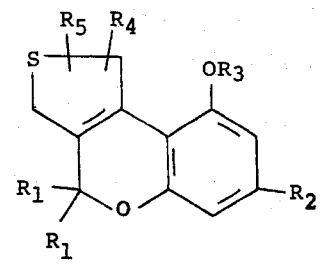

wherein $R_1$, $R_2$, $R_3$, $R_4$ and $R_5$ have the meanings assigned in claim 1.

4. A compound in accordance with claim 3 wherein for $R_3$, Y contains three or four carbons.

5. A compound in accordance with claim 4 named 1,3-dihydro-4,4-dimethyl-7-(3-methyl-2-octyl)-[4-(morpholino) butyryloxy]-4H-thieno[3,4-c][1]benzopyran or a nontoxic acid addition salt thereof.

6. A compound in accordance with claim 1 wherein $m$ is 0, $N$ is 2 and said compound is represented by the formula

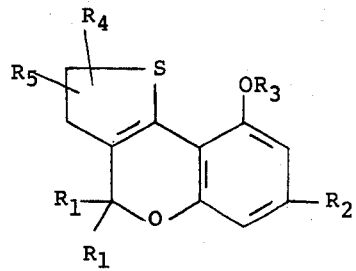

wherein $R_1$, $R_2$, $R_3$, $R_4$ and $R_5$ have the meaning assigned in claim 1.

7. A compound in accordance with claim 6 wherein for $R_3$, Y contains three or four carbons.

8. A compound in accordance with claim 7 named 2,3-dihydro-4,4-dimethyl-7-(3-methyl-2-octyl)-9-[4-(morpholino)butyryloxy]-4H-thieno[3,2-c][1]benzopyran or a nontoxic acid addition salt thereof.

9. A compound in accordance with claim 1 wherein $m$ is 1 and $n$ is 2 and said compound is represented by the formula

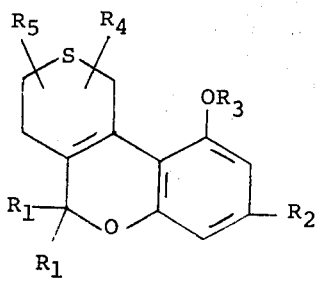

wherein $R_1$, $R_2$, $R_3$, $R_4$ and $R_5$ have the meaning assigned in claim 1.

10. A compound in accordance with claim 9 wherein for $R_3$, Y contains three or four carbons.

11. A compound in accordance with claim 10 named 3,4-dihydro-5,5-dimethyl-8-(3-methyl-2-octyl)-10-[4-(morpholino)butyryloxy]-1H,5H-thiopyrano[4,3-c][1]benzopyran or a nontoxic acid addition salt thereof.

12. A compound in accordance with claim 1 wherein m is 0, n is 3 and the compound is represented by the formula

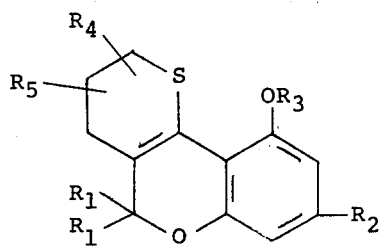

wherein $R_1$, $R_2$, $R_3$, $R_4$ and $R_5$ have the meaning assigned in claim 1.

13. A compound in accordance with claim 12 wherein for $R_3$, Y contains three or four carbons.

14. A compound in accordance with claim 1 wherein m is 2 and n is 0 and said compound is represented by the formula

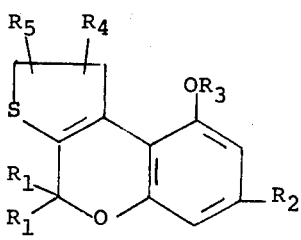

wherein $R_1$, $R_2$, $R_3$, $R_4$ and $R_5$ have the meaning assigned in claim 1.

15. A compound in accordance with claim 14 wherein for $R_3$, Y contains three or four carbons.

16. A compound in accordance with claim 15 named 1,2-dihydro-4,4-dimethyl-9-[4-(morpholino)-butyryloxy]-7-(3-methyl-2-octyl)-4H-thieno[2,3-c][1]benzopyran or a nontoxic acid addition salt thereof.

17. A compound in accordance with claim 15 named 1,2-dihydro-2,4,4-trimethyl-9-[4-(morpholino)-butyryloxy]-7-(3-methyl-2-octyl)-4H-thieno[2,3-c][1]benzopyran or a nontoxic acid addition salt thereof.

18. A compound in accordance with claim 1 wherein m is 2 and n is 1 and said compound is represented by the formula

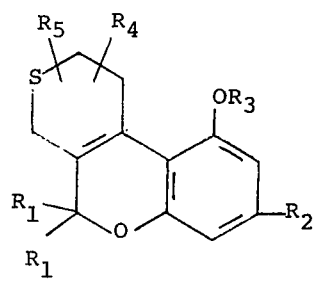

wherein $R_1$, $R_2$, $R_3$, $R_4$ and $R_5$ have the meaning assigned in claim 1.

19. A compound in accordance with claim 18 wherein for $R_3$, Y contains three or four carbons.

20. A compound in accordance with claim 1 wherein n is 0 and m is 3 and said compound is represented by the formula

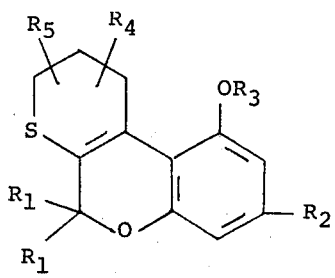

wherein $R_1$, $R_2$, $R_3$, $R_4$ and $R_5$ have the meaning assigned in claim 1.

21. A compound in accordance with claim 20 wherein for $R_3$, Y contains three or four carbons.

22. A compound in accordnce with claim 1 wherein Y contains three or four carbons, $R_1$ is methyl and $R_2$ is 3-methyl-2-octyl.

* * * * *

UNITED STATES PATENT AND TRADEMARK OFFICE
CERTIFICATE OF CORRECTION

PATENT NO. : 3,972,880
DATED : August 3, 1976
INVENTOR(S) : Louis Selig Harris et al.

It is certified that error appears in the above—identified patent and that said Letters Patent are hereby corrected as shown below:

Column 1, line 28, change "diloweralky" to --diloweralkyl--; column 3, line 14, before "when" insert --and--; line 30, put lower alkyl in quotation marks; line 36, put alkyl in quotation marks; line 42, put cycloalkyl in quotation marks; line 47, put acid addition salts in quotation marks; column 4, line 36, change "oxocompound" to -- oxo-compound --; line 49, insert --IX-- beneath the formula; line 59, insert --X-- beneath the formula; column 7, line 10, change "P." to --F.--; line 47, change "for form" to --to form--; column 8, line 49, change "2,5" to --2.5--; line 41, change "oxo2" to --oxo-2--; column 10, line 4, change "resorincol" to --resorcinol--; line 34, change "dimethyl9" to --dimethyl-9--; column 16, line 14, change "relfux" to --reflux--; line 59, after "γ" insert a dash (-); column 17, line 60, change "butyrola-" to -- butyrolac- --; line 64, after "21" insert a comma (,); column 18, last line, change "oo" to --oxo--; column 19, line 2, change "benzeneg." to --benzene/g.--; line 37, change "hydrochloroic" to --hydrochloric--; column 20, line 1, change "thiemo" to --thieno--; column 21, line 15, delete "obained" and before "-dihydro" insert --1,2--; column 22, line 19, change "22" to --2,2--; line 20, change "thiono" to --thieno--; column 23, line 50, change "85°c,10.1" to --85°C./0.1--; column 26, line 48, change "N" to --n--.

Signed and Sealed this

Nineteenth Day of October 1976

[SEAL]

Attest:

RUTH C. MASON
Attesting Officer

C. MARSHALL DANN
Commissioner of Patents and Trademarks